United States Patent

Yoshioka et al.

(10) Patent No.: US 8,680,314 B2
(45) Date of Patent: Mar. 25, 2014

(54) AMINO GROUP-CONTAINING PHOSPHORYLCHOLINE, AND METHOD FOR PRODUCING SAME

(75) Inventors: Nobuyuki Yoshioka, Tsukuba (JP); Nobuyuki Sakamoto, Tsukuba (JP); Yosuke Matsuoka, Tsukuba (JP); Norio Iwakiri, Tsukuba (JP)

(73) Assignee: NOF Corporation, Tokyo (JP)

( * ) Notice: Subject to any disclaimer, the term of this patent is extended or adjusted under 35 U.S.C. 154(b) by 0 days.

(21) Appl. No.: 13/997,304

(22) PCT Filed: Dec. 22, 2011

(86) PCT No.: PCT/JP2011/079825
§ 371 (c)(1),
(2), (4) Date: Jul. 30, 2013

(87) PCT Pub. No.: WO2012/086762
PCT Pub. Date: Jun. 28, 2012

(65) Prior Publication Data
US 2013/0310591 A1 Nov. 21, 2013

(30) Foreign Application Priority Data
Dec. 24, 2010 (JP) ................................. 2010-286981

(51) Int. Cl.
*C07F 9/02* (2006.01)
*C07F 9/06* (2006.01)
*C07F 9/08* (2006.01)
*C07F 9/09* (2006.01)
*C07F 9/10* (2006.01)

(52) U.S. Cl.
USPC .............................. 558/172; 558/70; 558/169

(58) Field of Classification Search
USPC ........................................................ 558/172
See application file for complete search history.

(56) References Cited

U.S. PATENT DOCUMENTS 6,828,029 B1 12/2004 Lewis et al.

FOREIGN PATENT DOCUMENTS

| EP | 0 486 100 A1 | 5/1992 |
|---|---|---|
| JP | 2004-500458 A | 1/2004 |
| JP | 2004-175676 A | 6/2004 |
| JP | 2006-008661 A | 1/2006 |
| JP | 2006-008987 A | 1/2006 |
| JP | 2008-189589 A | 8/2008 |
| WO | 2010/104167 A1 | 9/2010 |

OTHER PUBLICATIONS

Matsuno, R., "Simple synthesis of a library of zwitterionic surfactants via michael-type addition of methacrylate and alkane thiol compounds." Langmuir 26.16 (2010): 13028-13032.*

Sang-Ho Yea, et al., "Simple surface modification of a titanium alloy with silanated zwitterionic phosphorylcholine or sulfobetaine modifiers to reduce thrombogenicity" , Colloids and Surfaces B: Biointerfaces, Apr. 24, 2010, pp. 357-364, vol. 79.

Jian R. Lu, et al., "Reduced Protein Adsorption on the Surface of a Chemically Grafted Phospholipid Monolayer", Langmuir, 2001, pp. 3382-3389, vol. 17.

Ishihara K. Watanabe, et al., "Blood Compatible Cellulose Hollow Fibers Modified with MPC Polymer," Jpn J Artif Organs, 1994, pp. 654-659, vol. 23, No. 3.

* cited by examiner

*Primary Examiner* — Kortney L Klinkel
*Assistant Examiner* — John Mauro
(74) *Attorney, Agent, or Firm* — Sughrue Mion, PLLC

(57) ABSTRACT

Provided are amino group-containing phosphorylcholine compound and a method for production thereof, that has a highly active amino group efficiently reactive with a wide variety of functional groups and the like under mild conditions, and is capable of introducing a phosphorylcholine-like group to various substrate surfaces to provide functionalities of the group. The amino group-containing phosphorylcholine compound of the present invention is represented by at least one of formulae (1) and (1'), and may be used as a compound, or a material thereof, capable of introducing a phosphorylcholine-like group to the surface of various substrates, such as medical instruments, cosmetics materials, and medicinal substances.

4 Claims, 2 Drawing Sheets

AMINO GROUP-CONTAINING PHOSPHORYLCHOLINE, AND METHOD FOR PRODUCING SAME

FIELD OF ART

The present invention relates to an amino group-containing phosphorylcholine compound and a method for producing the same, which compound is capable of efficiently reacting with a variety of functional groups or the like, and is useful as a compound, or a raw material thereof, capable of introducing a phosphorylcholine-like group, for giving functionalities derived therefrom, to various substrates, such as medical instruments, cosmetics materials, and medicinal substances.

BACKGROUND ART

There have conventionally been proposed a number of techniques for providing a variety of substrates with various functionalities derived from a phosphorylcholine-like group, such as biocompatibility, moisture retaining ability, or water absorbability, by reacting a compound having a phosphorylcholine-like group with the surface of the substrates. For example, it is known that substrate surfaces treated with a various phosphorylcholine-like group compounds exhibit excellent biocompatibility, typically blood compatibility, and that medical instruments coated with polymers containing a phosphorylcholine-like group exhibit excellent biocompatibility (Non-patent Publication 1).

In an attempt to obtain a modifier for reacting a compound having a phosphorylcholine-like group with various substrate surfaces, compounds having a phosphorylcholine-like group into which a reactive group capable of reacting with various substrate surfaces have been introduced, have actively been developed as a modifier. For example, there are known a compound having a phosphorylcholine-like group with a silanol group introduced (Patent Publication 1), a compound having a phosphorylcholine-like group with a carboxyl group introduced (Patent Publication 2), a compound having a phosphorylcholine-like group with an aldehyde group introduced (Patent Publication 3), and a compound having a phosphorylcholine-like group with a ketal group introduced (Patent Publication 4).

In order to chemically bond, to a substrate surface, the compounds having a carboxyl or aldehyde group disclosed in Patent Publication 2 or 3, a functional group complementary to such group, such as an amino group, must be present on the substrate surface. In the absence of such an amino group, reaction rate is very low, so that long-time and high-temperature reaction conditions are required.

On the other hand, a substrate surface which has been subjected to, for example, plasma treatment or hydrolytic treatment to introduce a carboxyl group, which is industrially convenient, disadvantageously has low reactivity with the compounds having a phosphorylcholine-like group disclosed in Patent Publications 1 to 4.

In view of the above, it is industrially very beneficial to provide a compound having a phosphorylcholine-like group in to which a highly active (i.e., highly nucleophilic) amino or thiol group has been introduced, providing wide selectability of functional groups or the like on a substrate surface.

In this regard, Patent Publication 5 proposes a method in which 2-chloro-2-oxa-1,3,2-dioxaphospholane and trimethylamine are used.

However, production of a compound having a phosphorylcholine-like group with an amino group introduced by this method requires a step of protecting the amino group, which complicates the reactions and generates a large amount of byproducts. Thus this method has not been discussed in depth to date.

Patent Publication 1: JP-2006-8661-A
Patent Publication 2: JP-2006-8987-A
Patent Publication 3: JP-2004-175676-A
Patent Publication 4: JP-2008-189589-A
Patent Publication 5: EP-0486100-A
Non-patent Publication 1: Jpn J Artf Organs, Vol. 23(3), p 654-659 (1994)

SUMMARY OF THE INVENTION

It is an object of the present invention to provide an amino group-containing phosphorylcholine compound that has a highly active amino group efficiently reactive with a wide variety of functional groups and the like under mild conditions, and is useful as a compound, or a material thereof, capable of introducing a phosphorylcholine-like group to various substrate surfaces to provide functionalities of the group.

It is another object of the present invention to provide a method for producing the above-mentioned amino group-containing phosphorylcholine compound of the present invention that allows easy production of the compound at high yield without long-time and high-temperature reaction conditions.

The present inventors have made intensive researches for achieving the above objects, to find out that the amino group-containing phosphorylcholine compound may be obtained, starting with 2-methacryloyloxyethyl phosphorylcholine, of which production method has been established and which is industrially available, by adding to this starting material 2-aminoethanethiol and/or 2-aminoethanethiol hydrochloride at a particular ratio to induce the thiol group to preferentially undergo Michael addition reaction, to thereby complete the present invention.

According to the present invention, there is provided at least one amino group-containing phosphorylcholine compound represented by formula (1) and (1') (sometimes abbreviated as AmPC hereinbelow):

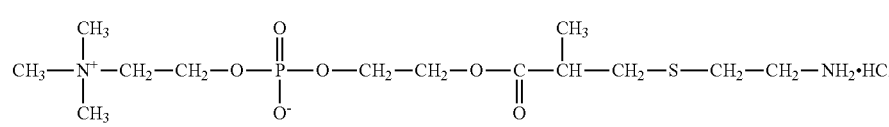

(1)

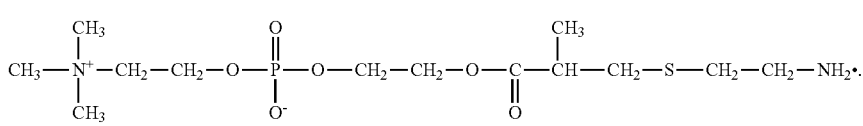

(1')

According to the present invention, there is also provided a method for producing the above-mentioned AmPC comprising reacting, in the presence of an alcohol:
(a) 2-methacryloyloxyethyl phosphorylcholine (abbreviated as MPC hereinbelow),
(b) 2-aminoethanethiol, and
(c) 2-aminoethanethiol hydrochloride,
at such a ratio that ((b)+(c))/(a) is 1.0 to 3.0 mole equivalents and (b)/(c) is 0.05 to 1.00 mole equivalent.

According to the present invention, there is further provided a method for producing AmPC comprising reacting, in the presence of an alcohol, (a) MPC and (b) 2-aminoethanethiol or (c) 2-aminoethanethiol hydrochloride, at such a ratio that ((b)+(c))/(a) is 1.0 to 3.0 mole equivalents.

AmPC according to the present invention has a structure represented by formula (1) and/or (1') and having a phosphorylcholine-like group and a highly active amino group, and thus may be bound to a variety of functional groups, such as carboxyl, aldehyde, or isocyanate group or halogen, under mild conditions at a high reaction rate. Therefore, AmPC is useful as a compound, or a material thereof, that introduces a phosphorylcholine-like group to a surface of various substrates, such as medical instruments, cosmetics materials, or medicinal substances. Further, when used as a component of a surface treatment agent, AmPC may easily provide a substrate with its functionalities. For example, by using AmPC of the present invention in introducing a phosphorylcholine-like group to the surface of a medical instrument for improving its biocompatibility, selectivity of materials for medical instruments may be expanded, and the introduction of a phosphorylcholine-like group may become easier.

The production method according to the present invention requires reaction of MPC with 2-aminoethanethiol and/or 2-aminoethanetiol hydrochloride at a particular ratio, so that production of AmPC is attained under mild conditions at a high yield. In particular, by reacting MPC, 2-aminoethanethiol, and 2-aminoethanethiol hydrochloride at a particular ratio, AmPC represented by formula (1) may be obtained at a still higher yield.

EMBODIMENTS OF THE INVENTION

Figure 1:
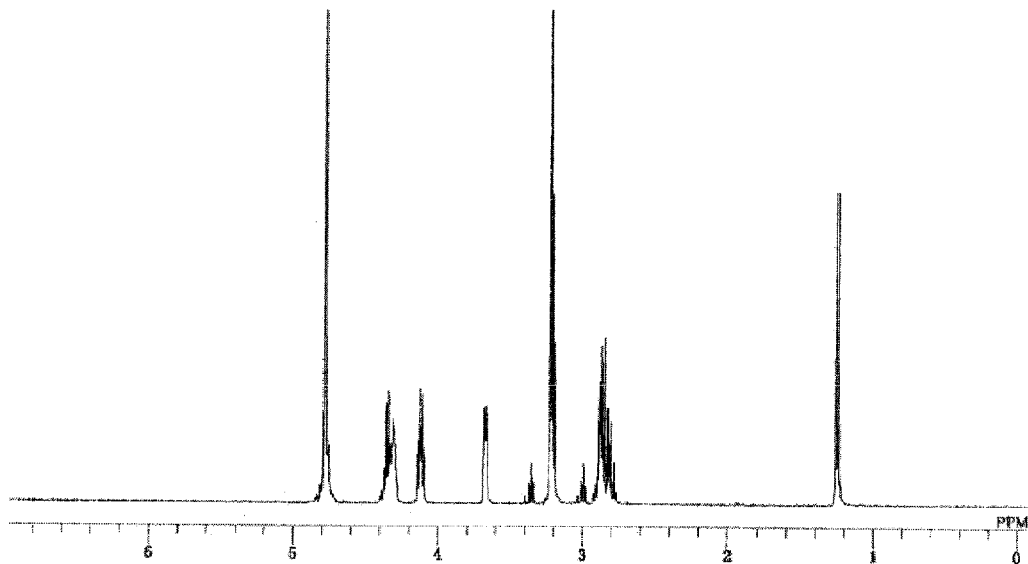
FIG. 1 is a chart showing the result of $^1$H-NMR measurement of a compound synthesized in Example 1.

The present invention will now be explained in detail.
The amino group-containing phosphorylcholine compound (AmPC) according to the present invention is 2'-[3-(2-aminoethylsulfanil)-2-methylpropionyloxy]ethyl 1-[2-(trimethylammonio)ethyl]phosphate hydrochloride represented by formula (1) and/or 2'-[3-(2-aminoethylsulfanil)-2-methylpropionyloxy]ethyl 1-[2-(trimethylammonio)ethyl]phosphate represented by formula (1').

AmPC according to the present invention may be prepared, for example, by a production method according to the present invention, wherein (a) MPC and (b) 2-aminoethanethiol and/or (c) 2-aminoethanethiol hydrochloride are reacted at a particular ratio in the presence of an alcohol.

(a) MPC is a compound represented by formula (2), (b) 2-aminoethanethiol is a compound represented by formula (3), and (c) 2-aminoethanethiol hydrochloride is a compound represented by formula (4):

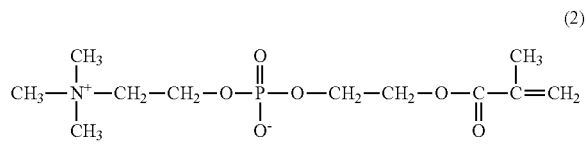

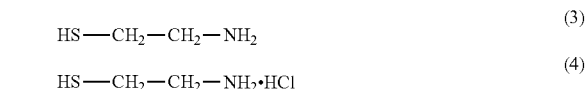

In the method for producing AmPC of the present invention, when all of the starting monomers (a) to (c) are used, the charging ratio of the monomers is preferably such that ((b)+(c))/(a) is 1.0 to 3.0 mole equivalents and (b)/(c) is 0.05 to 1.00 mole equivalent (collectively referred to as ratio (X) hereinbelow).

On the other hand, in the method for producing AmPC of the present invention, when the starting monomers (a) and (b) or (c) are used, the charging ratio of the monomers is preferably such that ((b)+(c))/(a) is 1.0 to 3.0 mole equivalents (referred to as ratio (Y) hereinbelow).

In ratios (X) and (Y), when ((b)+(c))/(a) exceeds 3.0 mole equivalents, the amino group may be subjected to Michael addition reaction or MPC may be decomposed.

According to the method for producing AmPC of the present invention wherein the starting monomers are reacted at ratio (X), a reaction product may be obtained at significantly high purity without a catalyst such as diisopropylamine described, for example, in Langmuir, 2010, 26(16), p 13028-13032.

The alcohol used in the method for producing AmPC according to the present invention acts as a solvent for dissolving the starting monomers, which are all in solid forms, for reaction. The alcohol may be, for example, methanol or ethanol, with ethanol being preferred for its reactivity and low toxicity. The amount of the alcohol used is not particularly limited as long as the starting monomers are dissolved, and preferably adjusted so that the concentration of the solution for reaction is 10 to 50 mass %.

According to the method for producing AmPC of the present invention, the reaction is preferably carried out in an atmosphere of an inert gas, such as nitrogen or argon, so as to prevent the thiol group from forming disulfide and to keep the nucleophilicity of the thiol group. If the reaction temperature exceeds 50° C., the amino group undergoes Michael addition reaction with the double bond as a side reaction, or the thiol group may form disulfide, resulting in a lower yield of the objective AmPC. Thus, the reaction temperature is preferably 10 to 50° C. The reaction time may be arbitrary, but a reaction for a long period of time involves oxidation degradation, so that the reaction time is preferably within 96 hours.

According to the method for producing AmPC of the present invention, the reaction may be carried out in the presence of a catalyst for obtaining a reaction product having a higher inversion rate and suppressing production of byproducts. This is particularly preferred for the method wherein the reaction is effected at ratio (Y).

The catalyst in this case may be, for example, a tertiary or secondary amine. The tertiary amine may be triethylamine, and the secondary amine may be diisopropylamine.

The amount of the catalyst may usually be 5 to 100 mol % with respect to the amount of 2-aminoethanethiol and/or 2-aminoethanethiol hydrochloride.

The product obtained by the method of the present invention is preferably purified depending on its application. For example, for high safety applications such as medical instruments or cosmetics, the product is preferably highly purified. The purification may be performed by crystallization in an aprotic polar solvent such as acetonitrile, followed by drying and collecting, or by precipitation in a solvent such as acetone or acetonitrile, followed by collection, washing, removal of the solvent by distillation, and collection.

AmPC of the present invention, having an amino group, may be chemically bonded to other substances by condensation, nucleophilic displacement, addition, conjugated displacement, reductive amination, or the like reaction. Examples of the combination and the reaction are shown in Table 1.

TABLE 1

| Reaction | Reagent | Resulting bond or functional group |
| --- | --- | --- |
| Condensation | Carboxylic compound | Amide bond |
| | Acid anhydride | |
| | Acid halide | |
| | Amino acid | |
| Nucleophilic displacement | Aldehyde compound | Imine derivative |
| | Carbonyl compound | Imine derivative |
| | Epoxide compound | 1,2-amino alcohol derivative |
| | Halide | Secondary amine, Tertiary amine |
| | Isocyanate compound | Urea derivative |
| Addition | Cyano group-containing compound | Amidine derivative Guanidine derivative |
| Conjugated displacement | Unsaturated cyano group-containing compound | Amidine derivative Guanidine derivative |
| | Unsaturated nitro group-containing compound | |
| Reductive amination | Aldehyde compound | Imine derivative, Secondary amine |

AmPC of the present invention may be used for surface modification treatment of various medical instruments such as soft contact lenses or catheter, surface modification treatment of cosmetic materials such as foundation, surface modification of proteins or biomaterials, or improvement of drug delivery performance by binding to medicinal substances. Specifically, when AmPC is used for surface modification treatment of a medical instrument, for example, contact lenses, a phosphorylcholine-like group may be introduced to the lens surface, on which carboxyl groups predominantly exist, by activation of these carboxyl groups with 1-ethyl-3-(3-dimethylaminopropyl)carbodiimide hydrochloride (EDC), dicyclohexylcarbodiimide (DCC), or the like, and addition reaction of AmPC of the present invention therewith. In this way, the functionalities of a phosphorylcholine-like group, for example, antifouling property such as protein adsorption inhibitory property, may easily be given to the contact lenses.

EXAMPLES

The present invention will now be explained in detail with reference to Examples, which do not intend to limit the present invention.

Apparatus and conditions used in Examples are described below.

<NMR Analysis>
Measuring apparatus: JNM-AL 400 manufactured by JEOL LTD.
Solvent: $D_2O$ (0.0005% in terms of 3-(trimethylsilyl)propionic acid sodium salt)
Sample Concentration: 10 mg/g
Cumulated number: 32 times ($^1$H-NMR), 1024 times ($^{13}$C-NMR)<
<IR Analysis>
Measuring apparatus: FT/IR-6100 manufactured by JASCO CORPORATION
Measurement method: Thin film method
Cumulated number: 16 times
<Mass Spectrometry (ESI-MS)>
Measuring apparatus: trade name Q-micro2695, manufactured by NIHON WATERS K.K.
Sample concentration: 100 ppm; Detection mode: ESI+;
Capillary voltage: 3.54V; Cone voltage: 30V;
Ion source heater: 120° C.; Desolvation gas: 350° C.

Example 1-1

Synthesis of 2'-[3-(2-aminoethylsulfanil)-2-methyl-propionyloxy]ethyl-[2-(trimethylammonio)ethyl] phosphate hydrochloride (AmPC)

2.00 g (6.77 mmol) of MPC was placed in a three-neck flask, to which 11.33 g of ethanol was added and stirred into a homogeneous mixture. The mixture was bubbled with nitrogen gas to establish a nitrogen atmosphere in the flask, to which 0.80 g (7.08 mmol) of 2-aminoethanethiol hydrochloride was added, and dissolved into a homogeneous mixture. Then 0.03 g (0.37 mmol) of 2-aminoethanethiol was added, and stirred at room temperature for 3 hours to react. To the obtained reaction solution was added 11.33 g of acetonitrile, and the solvent was removed by azeotropic distillation under reduced pressure, to thereby obtain a white solid product.

Figure 2:
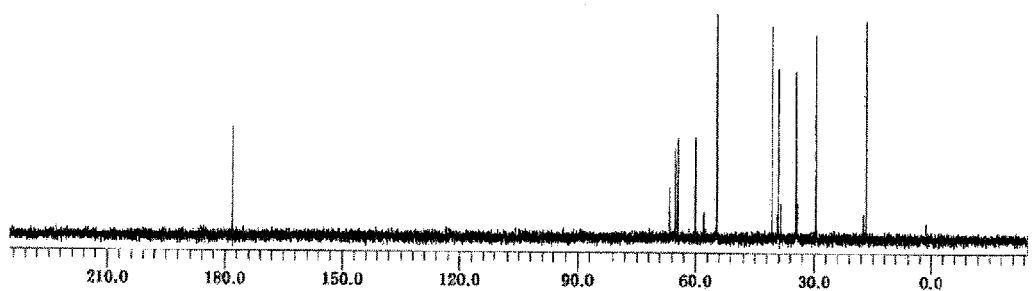
FIG. 2 is a chart showing the result of $^{13}$C-NMR measurement of a compound synthesized in Example 1.
Figure 3:
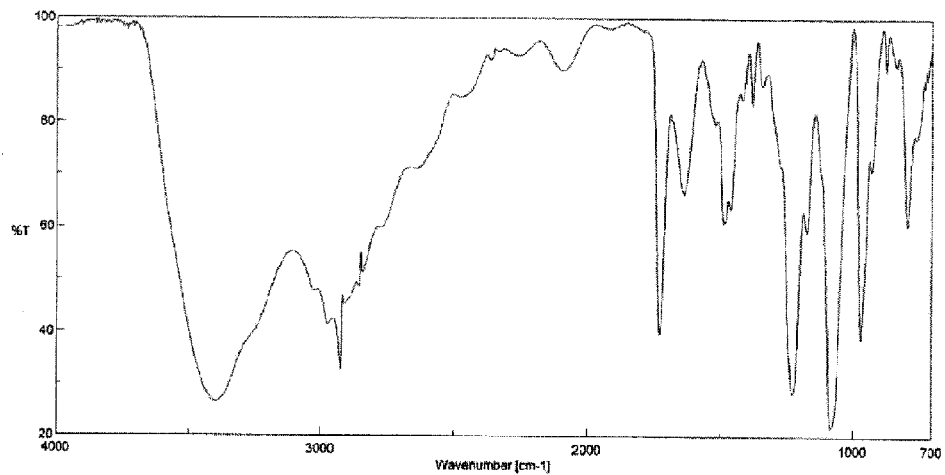
FIG. 3 is a chart showing the result of IR measurement of a compound synthesized in Example 1.
Figure 4:
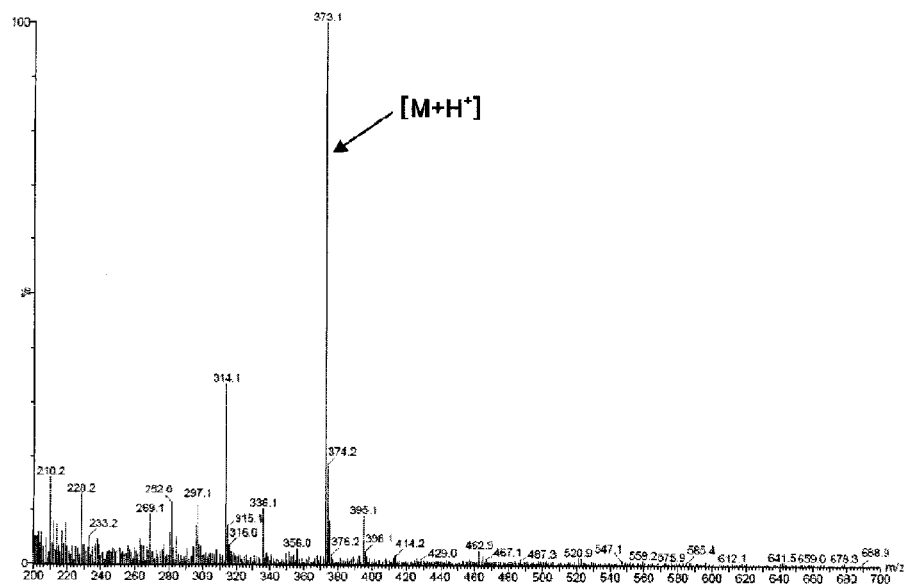
FIG. 4 is a chart showing mass spectra of a compound synthesized in Example 1.

The obtained white solid product was subjected to $^1$H-NMR analysis, $^{13}$C-NMR analysis, IR analysis, and mass spectrometry. The results are shown in FIGS. 1 to 4 and below. The results demonstrated that the obtained white solid product was the objective compound AmPC represented by formula (1).

Peaks observed in $^1$H-NMR spectra were identified by reference to Langmuir, 2010, 26(16), p 13028-13032. The peaks observed in $^{13}$C-NMR spectra were identified by reference to Polymer Journal, 1990, 22(5), p 355-360.

$^1$H-NMR ($D_2O$): δ=1.2 (—CH($CH_3$)C(=O), 3H), 2.8-2.9 (—($CH_3$) CH$CH_2$S$CH_2$$CH_2$—, 5H), 3.2 ((—$CH_2$$NH_2$, 2H)

(—N(CH₃), 9H)), 3.7 (N(CH₃)CH₂—, 2H), 4.1 (—CH₂OP—, 2H), 4.3-4.4 (—POCH₂CH₂O—, 4H).

¹³C-NMR (D₂O): δ=16.6 (—CH(CH₃)C(=O)), 29.6 (—CH₂SCH₂CH₂NH₂), 34.6 (—CH₂SCH₂CH₂NH₂), 39.1 (—CH(CH₃)C(=O)), 40.6 (—SCH₂CH₂NH₂), 54.6 (—N(CH₃)), 60.0 (CH₂N(CH₃)), 64.4 (NCH₂CH₂OP), 65.1 (-OCH₂CH₂O—), 66.2 (-OCH₂CH₂O—), 178.1 (C=O).

Peaks observed in IR spectra were identified by reference to Langmuir, 2010, 26(16), p 13028-13032.

FT-IR (cm⁻¹): 3393 (—NH₃⁺), 2924 (C—H), 1727 (C=O), 1226 (C=O), 1082 (—OPOCH₂—), 967 (—N⁺(CH₃)₃—).

Based on the values of integral obtained from the ¹H-NMR analysis, purity of AmPC and the byproduct ratio were calculated according to the following manner. As a result, it was found that purity of AmPC was 100%, and the byproduct content was 0%. The results are shown in Table 2.

Purity of AmPC (%)=value of integral at 4.1 ppm/
  [(value of integral at 1.9 ppm+value of integral at
  1.2 ppm)×2/3]×inversion rate Inversion rate (%)=100−(MPC content)

MPC content (%)=[1−value of integral at 1.9 ppm/
  (value of integral at 1.9 ppm+value of integral at
  1.2 ppm)]×100

Byproduct ratio (%)=inversion rate−(purity of AmPC)

Examples 1-2 to 1-4

A product was obtained through the reaction, analyzed, and measured in the same way as in Example 1-1 except that the charging ratio of the starting materials and the conditions were changed as shown in Table 2. The results are shown in Table 2.

TABLE 2

|  | Example 1-1 | Example 1-2 | Example 1-3 | Example 1-4 |
|---|---|---|---|---|
| (a) MPC | 6.77 mmol | 6.77 mmol | 6.77 mmol | 6.77 mmol |
| (b) 2-amino-ethanethiol | 0.37 mmol | 0.75 mmol | 1.86 mmol | 3.73 mmol |
| (c) 2-amino-ethanethiol hydrochloride | 7.08 mmol | 6.71 mmol | 5.59 mmol | 3.73 mmol |
| ((b) + (c))/(a) | 1.10 | 1.10 | 1.10 | 1.10 |
| (b)/(c) | 0.05 | 0.11 | 0.33 | 1.00 |
| Solvent | ethanol | ethanol | ethanol | ethanol |
| Amount of solvent | 11.33 g | 11.58 g | 11.40 g | 11.10 g |
| Temperature | 25° C. | 25° C. | 25° C. | 25° C. |
| Reaction Time | 3 hours | 3 hours | 3 hours | 3 hours |
| Purity |  |  |  |  |
| Main product | 100% | 100% | 100% | 100% |
| Residual MPC | 0% | 0% | 0% | 0% |
| Byproducts etc. | 0% | 0% | 0% | 0% |

Examples 1-5 to 1-8

A product was obtained through the reaction, analyzed, and measured in the same way as in Example 1-1 except that the charging ratio of the starting materials and the conditions were changed as shown in Table 3. As a catalyst, diisopropylamine and triethylamine were used in Examples 1-5 and 1-6, respectively. The results are shown in Table 3. As a result of the analyses, the main products obtained in Examples 1-7 and 1-8 were both 2'-[3 (2-aminoethylsulfanil)-2-methylpropionyloxy]ethyl-[2-trimethylammonio]ethyl]phosphate.

TABLE 3

|  | Example 1-5 | Example 1-6 | Example 1-7 | Example 1-8 |
|---|---|---|---|---|
| (a) MPC | 6.77 mmol | 6.77 mmol | 6.77 mmol | 6.77 mmol |
| (b) 2-amino-ethanethiol | — | — | 8.13 mmol | 20.32 mmol |
| (c) 2-amino-ethanethiol hydrochloride | 8.13 mmol | 8.13 mmol | — | — |
| ((b) + (c))/(a) | 1.20 | 1.20 | 1.20 | 3.00 |
| (d1) Diisopropyl-amine | 0.34 mmol | — | — | — |
| (d2) Triethyl-amine | — | 0.34 mmol | — | — |
| (d)/(c) | 0.05 | 0.05 | — | — |
| Solvent | Ethanol | Ethanol | Methanol | Methanol |
| Amount of solvent | 11.69 g | 11.58 g | 11.69 g | 14.27 g |
| Temperature | 25° C. | 25° C. | 25° C. | 25° C. |
| Reaction Time | 6 hours | 6 hours | 6 hours | 6 hours |
| Purity |  |  |  |  |
| Main product | 81% | 78% | 72% | 50% |
| Residual MPC | 5% | 7% | 6% | 0% |
| Byproducts etc. | 14% | 15% | 22% | 50% |

As shown in the above, it was confirmed that the objective AmPC may be obtained at a high yield according to the production method of the present invention. It was demonstrated that, when a mixture of 2-aminoethanethiol hydrochloride and 2-aminoethanethiol at a particular ratio was used as the starting material (Examples 1-1 to 1-4), the reaction proceeded significantly efficiently under mild conditions without byproducts being produced.

Example 2-1

Using the amino group-containing phosphorylcholine compound obtained by the synthesis in Example 1-1, introduction of a phosphorylcholine group to a substrate having a carboxylic group on its surface was attempted. As the substrate having carboxylic acid, a PE film having acrylic acid introduced on its surface by graft polymerization was selected, and reacted with the amino group-containing phosphorylcholine compound using a condensation agent, 1-ethyl-3-(3-dimethylaminopropyl) carbodiimide hydrochloride (WSC). The reacted film was analyzed by X-ray photoelectron spectroscopy (XPS) for introduction of the phosphorylcholine group. The process employed is discussed below.

Preparation of Acrylic Acid (AA)-Grafted Polyethylene (PE) Film

A polyethylene film cut into a 1×4 cm piece was placed between electrodes of a corona discharge device with the interelectrode distance of 3 cm at a voltage between the electrodes of 15 kV, and subjected to discharge treatment. Then the film was soaked in a 10 mass % aqueous solution of acrylic acid, and after deaeration, graft polymerization was effected in vacuo at 60° C. for 60 minutes. After the polymerization, the film was sufficiently washed with water, and an AA-grafted PE film was obtained.

Preparation of Phosphorylcholine Group-Introduced Film

In a 15 cc polypropylene tube, 0.1464 mmol of WSC and 0.1464 mmol of AmPC synthesized in Example 1-1 were placed, and dissolved in ion-exchanged water added thereto, into a uniform mixture, in which the AA-grafted film cut into a 0.5 cm×0.5 cm piece was placed. The mixture with the film was transferred to a thermostatic chamber with stirring function, and reacted under stirring at 30° C. for 24 hours. The reacted film was taken out, and washed three times with 5 mL of ion-exchanged water to remove excess WSC and unreacted AmPC. After drying, a phosphorylcholine group-introduced film was obtained.

The obtained film was subjected to surface analysis by XPS to determine the ratio of AmPC introduced. The film was also evaluated for surface wettability in order to confirm whether the surface had been made hydrophilic by the introduction of the phosphorylcholine group.

XPS Evaluation

The surface of the 0.5 cm×0.5 cm film sample obtained above was evaluated for elemental concentration with an X-ray photoelectron spectroscope (XPS, JPS-9200 manufactured by JEOL LTD.) (diameter for analysis: 1 mm). Each sample was analyzed for the bond energy of 304 eV to 274 eV (carbon is orbital), 419 eV to 389 eV (phosphorus 2p3/2 orbital), 155 eV to 125 eV (nitrogen is orbital), and 184 eV to 154 eV (sulfur 2p3/2 orbital), and the ratio of AmPC introduced was calculated.

The ratio of AmPC introduced was calculated from the surface concentrations of phosphorus atoms ($C_P$) and carbon atoms ($C_C$) in accordance with following formula (A):

$$\text{Ratio introduced (\%)} = \frac{C_P}{C_C} \times \frac{1}{6.25} \times 100 \quad (A)$$

Evaluation of Surface Wettability

The film (0.5 cm×0.5 cm) obtained above was soaked in 100 mL of pure water for 30 seconds, and then vertically lifted up into the air with tweezers. At this time, the film was measured under visual observation for the time taken until the water film was broken to expose the surface (water break-up time: WBUT). The following scores were given depending on the WBUT values to evaluate the surface wettability.

Surface Wettability Evaluation Score
 3 points: WBUT>20 seconds
 2 points: WBUT=10 to 19 seconds
 1 point: WBUT=5 to 9 seconds
 0 point: WBUT=0 to 4 seconds As the number of seconds of WBUT is larger, the tendency to hydrophilicity is higher.

As a result of the XPS analysis, AmPC was introduced to the filmprepared in Example 2-1 at 14.9%. In the surface wettability evaluation, the film got 3 points, indicating that the film had surface hydrophilicity.

Referential Example 2-1

A film was prepared through the reaction, analyzed, and evaluated in the same way as in Example 2-1 except that the film used and the amount of solvent were changed as shown in Table 4. The results are shown in Table 4.

TABLE 4

|  | Example 2-1 | Referential Example 2-1 |
|---|---|---|
| Film used | AA-grafted PE | PE |
| Film area | 0.25 cm² | 0.25 cm² |
| Amount of carboxylic acid in film | 0.0146 mmol | 0 mmol |

TABLE 4-continued

|  | Example 2-1 | Referential Example 2-1 |
|---|---|---|
| WSC | 0.1464 mmol | 0.1464 mmol |
| AmPC of Example 1-1 | 0.1464 mmol | 0.1464 mmol |
| Water | 8.424 g | 8.424 g |
| Ratio of AmPC introduced |  |  |
| Theoretical | 100% | 0% |
| Measured | 14.9% | 0% |
| WBUT | >20 seconds | 0 second |
| Wettability evaluation | 3 | 0 |

In this way, it was confirmed that AmPC was introduced to the film surface. AmPC was introduced particularly to the film having carboxylic acid on its surface. As a result, it was demonstrated that the water wettability of the film surface may be improved. It is conceivable that the amino group-containing phosphorylcholine compound obtained by the present invention, making the most of such property, may be applied to medical instruments, such as contact lenses or catheters, and the treated medical instruments may be expected to have improved surface wettability and excellent biocompatibility due to the phosphorylcholine groups on their surfaces.

What is claimed is:

1. An amino group-containing phosphorylcholine compound represented by the formulae (1) or (1')

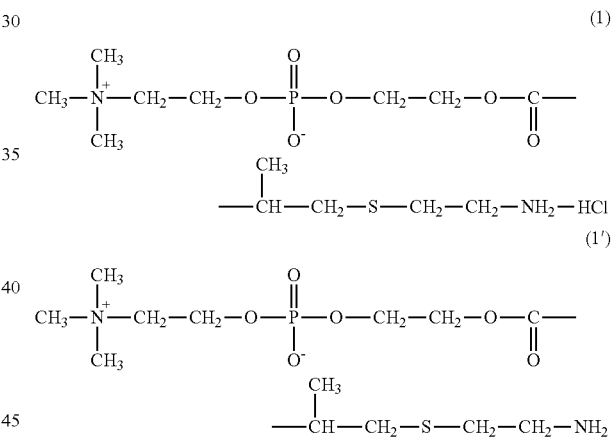

or a mixture of the compound represented by formula (1) and the compound represented by formula (1').

2. A method for producing an amino group-containing phosphorylcholine compound according to claim 1, comprising reacting, in the presence of an alcohol, (a) 2-methacryloyloxyethyl phosphorylcholine, (b) 2-aminoethanethiol, and (c) 2-aminoethanethiol hydrochloride at such a ratio that ((b)+(c))/(a) is 1.0 to 3.0 mole equivalents and (b)/(c) is 0.05 to 1.00 mole equivalent.

3. A method for producing an amino group-containing phosphorylcholine compound according to claim 1, comprising reacting, in the presence of an alcohol, (a) 2-methacryloyloxyethyl phosphorylcholine and (b) 2-aminoethanethiol and (c) 2-aminoethanethiol hydrochloride at such a ratio that ((b)+(c))/(a) is 1.0 to 3.0 mole equivalents.

4. The method according to claim 3, wherein said reaction is effected in the presence of a catalyst.

* * * * *